US005792058A

United States Patent [19]

Lee et al.

[11] Patent Number: 5,792,058

[45] Date of Patent: Aug. 11, 1998

[54] BROADBAND PHASED ARRAY TRANSDUCER WITH WIDE BANDWIDTH, HIGH SENSITIVITY AND REDUCED CROSS-TALK AND METHOD FOR MANUFACTURE THEREOF

[75] Inventors: Wendy J. Lee, Cupertino; John William Sliwa, Jr., Palo Alto; Sevig Ayter, Cupertino; Amin Hanafy, Los Altos Hills, all of Calif.

[73] Assignee: Acuson Corporation, Mountain View, Calif.

[21] Appl. No.: 731,000

[22] Filed: Oct. 16, 1996

Related U.S. Application Data

[63] Continuation of Ser. No. 480,676, Jun. 7, 1995, abandoned, which is a continuation-in-part of Ser. No. 117,869, Sep. 7, 1993, Pat. No. 5,438,998.

[51] Int. Cl.[6] .................... A61B 8/00

[52] U.S. Cl. .................... 600/459

[58] Field of Search .................... 128/660.08, 660.1, 128/661.01, 662.03; 29/25.35; 310/327, 334, 335; 73/632, 633; 600/444, 446, 447, 459

[56] References Cited

U.S. PATENT DOCUMENTS

| | | | |
|---|---|---|---|
| 4,016,751 | 4/1977 | Kossoff . | |
| 4,184,094 | 1/1980 | Kopel . | |
| 4,205,686 | 6/1980 | Harris et al. . | |
| 4,276,491 | 6/1981 | Daniel . | |
| 4,277,712 | 7/1981 | Hanafy . | |
| 4,350,917 | 9/1982 | Lizzi et al. . | |
| 4,384,228 | 5/1983 | Dias . | |
| 4,478,085 | 10/1984 | Sasaki . | |
| 4,550,607 | 11/1985 | Maslak et al. . | |
| 4,564,980 | 1/1986 | Diepers . | |
| 4,686,408 | 8/1987 | Ishiyama . | |
| 4,699,150 | 10/1987 | Kawabuchi et al. . | |
| 4,734,963 | 4/1988 | Ishiyama . | |
| 4,773,140 | 9/1988 | McAusland . | |
| 4,869,768 | 9/1989 | Zola . | |
| 4,939,826 | 7/1990 | Shoup . | |
| 4,992,692 | 2/1991 | Dias . | |
| 5,042,492 | 8/1991 | Dubut . | |
| 5,042,493 | 8/1991 | Saito et al. . | |
| 5,044,053 | 9/1991 | Kopel et al. . | |
| 5,163,436 | 11/1992 | Saitoh et al. . | |
| 5,291,090 | 3/1994 | Dias . | |
| 5,295,487 | 3/1994 | Saitoh et al. . | |
| 5,423,220 | 6/1995 | Finsterwald et al. . | |
| 5,467,779 | 11/1995 | Smith et al. | 128/660.1 |

FOREIGN PATENT DOCUMENTS

| | | |
|---|---|---|
| 0346891 | 12/1989 | European Pat. Off. . |
| 54-149615 | 11/1979 | Japan . |
| 64-68981 | 3/1989 | Japan . |
| 2079456 | 1/1982 | United Kingdom . |
| 2190818 | 11/1987 | United Kingdom . |

*Primary Examiner*—George Manuel
*Attorney, Agent, or Firm*—Brinks Hofer Gilson & Lione

[57] ABSTRACT

There is provided a broadband transducer array for use in an acoustic imaging system having a plurality of transducer elements disposed on a preformed support. The support has a non-planar top surface on which are disposed a plurality of elevationally curved transducer elements. Kerfs separate each transducer element from one another. The depth of the kerf with reference to the non-planar top surface of the support may be uniform or non-uniform.

23 Claims, 8 Drawing Sheets

BROADBAND PHASED ARRAY TRANSDUCER WITH WIDE BANDWIDTH, HIGH SENSITIVITY AND REDUCED CROSS-TALK AND METHOD FOR MANUFACTURE THEREOF

This application is a continuation of application Ser. No. 08/480,676, filed Jun. 7, 1995, now abandoned which is a continuation-in-part of application U.S. Ser. No. 08/117,869 filed Sep. 7, 1993, now U.S. Pat. No. 5,438,998, entitled "Broadband Phased Array Transducer Design With Frequency Controlled Two Dimension Capability and Methods for Manufacture Thereof" by A. Hanafy.

FIELD OF THE INVENTION

This invention relates to transducers and more particularly to broadband phased array transducers for use in the medical diagnostic field.

Ultrasound machines are often used for observing organs in the human body. Typically, these machines incorporate transducer arrays for converting electrical signals into pressure waves and vice versa. Generally, the transducer array is in the form of a hand-held probe which may be adjusted in position while contacting the body to direct the ultrasound beam to the region of interest. Transducer arrays may have, for example, 128 phased transducer segments or elements for generating a steerable ultrasound beam in order to image a sector slice of the body.

Electrical contact is made to the front and rear portion of each transducer element for individually exciting and receiving from each element. The pressure waves generated by the transducer elements are directed toward the object to be observed, such as the heart of a patient being examined. The steering of the beam in the plane of electronic scanning, i.e., the image plane, is done in real time by computer generated time delays. Each time a pressure wave confronts a tissue interface having different acoustic impedance characteristics, a wave is reflected backward. The phased array of transducer segments may then likewise convert the reflected pressure waves into corresponding electrical signals. An example of a phased array acoustic imaging system is described in U.S. Pat. No. 4,550,607 granted Nov. 5, 1985 to Maslak et al. and is incorporated herein by reference. That patent illustrates circuitry for focusing the incoming signals received by the transducer array in order to produce an image on the display screen.

Broadband transducers are transducers capable of operating over a wide range of frequencies without a loss in sensitivity. In general higher frequencies give better resolution but are attenuated more. Thus, a broadband array is desired to provide high frequencies for imaging the shallow nearfield and lower frequencies for imaging the deeper tissue.

The dimension of a phased array transducer orthogonal to the electronically scanned azimuthal plane is referred to as the elevational dimension or axis. There is normally only nonelectronic passive focusing in this slice-thickness dimension.

The elevation focusing of most phased array transducers can generally be categorized as lens focused or mechanically focused. In the case of lens focused transducer arrays the emitting surface of the array is flat in the elevation direction and a shaped material, the lens material, is placed between the object to be imaged and the array. The lens material has a different velocity of sound than the object being imaged. The elevational focusing of the ultrasound beam is achieved through refraction at the lens/object interface. U.S. Pat. Nos. 4,686,408 and 5,163,436 describe lens focused phased array transducers and are specifically incorporated herein by reference. The material used to form the lens is typically silicone based and, unfortunately, also has the undesirable property of absorbing or attenuating passing ultrasound energy and thereby reducing the overall sensitivity of the transducer array.

Mechanically focused transducer arrays utilize a piezoelectric layer which has a curved surface which faces the object to be imaged. The surface is curved along the elevation direction and forms either a concave or convex structure. U.S. Pat. Nos. 4,184,094 and 4,205,686 describe such mechanically focussed transducer arrays and are hereby specifically incorporated by reference. Several methods have been employed to form the elevation curvature in the piezoelectric layer including machining the piezoelectric layer or employing bendable or formable composite piezoelectric materials. U.S. Pat. No. 4,869,768 describes dicing the top and bottom of a large piezoelectric blank, filling the diced kerfs with resin material, partially curing the resin material and then forming the desired curved shape during which a full cure of the resin is achieved. This curved composite is then finish-ground to remove one of the undiced layers and to achieve the desired thickness.

Another method of forming a mechanically focused transducer array is disclosed in PCT Publication No. WO 94/16826 published Aug. 4, 1994 and specifically incorporated herein by reference. The method includes forming an intermediate assembly by applying one or more acoustic matching layers to a concave front surface of a piezoelectric substrate. The intermediate assembly is affixed to a temporary flexible front carrier plate and a series of substantially parallel cuts are made completely through the intermediate assembly and into the flexible front carrier plate. The cuts form a series of individual transducer elements. Next, the intermediate assembly is formed into a desired shape by bending the layers against the yielding bias of the flexible front carrier plate. The shaped intermediate assembly is then affixed to a backing support adjacent the rear surface of the piezoelectric substrate and the temporary front carrier plate is removed yielding the ultrasonic transducer array.

A disadvantage of lens focused transducer arrays is that materials which have the proper acoustic velocity for use as a lens, such as silicone rubbers, often absorb significant amounts of acoustic energy both on transmit and receive, thus reducing the signal strength of the reflections. The amount of absorption is frequency dependent with higher frequencies being attenuated more. Another drawback of the silicone based material is its impedance is not well matched to the human body, hence resulting in reverberation artifacts in the image.

A disadvantage of mechanically focused transducer arrays is that they are relatively complicated to manufacture. Often, several temporary substrates, some of which require several processing steps to prepare are needed. These temporary substrates complicate the process due to the fact that they need to be attached and then removed which involves several processing and cleaning steps.

It is thus desirable to provide a method of manufacturing a transducer array having a minimal number of steps which does not require complex or intricate processing. It is also desirable to provide a method of manufacturing a transducer array in a quick and simple manner to produce high yields.

SUMMARY OF THE INVENTION

According to a first aspect of the present invention there is provided a transducer array for producing an ultrasound beam upon excitation. The transducer array includes a backing block, a signal flex circuit, a piezoelectric layer and ground flex circuit. The backing block has a non-planar curved, top surface in the elevation direction. The signal flex circuit is disposed over the non-planar curved top surface. The piezoelectric layer has a first surface coupled to the signal flex circuit and has a plurality of bending kerfs extending partially into the piezoelectric layer. The plurality of bending kerfs extend in an azimuthal direction and allow curvature of the piezoelectric layer in the elevational direction. A ground flex circuit is coupled to a second opposing surface of the piezoelectric layer.

According to a second aspect of the present invention there is provided a method of constructing a transducer. The method includes providing a backing block having a non-planar top surface, attaching a first surface of a layer of piezoelectric material to a first flex circuit, dicing parallel slots in the layer of piezoelectric material along an azimuthal direction, bending the layer of piezoelectric material in an elevation direction, and attaching a second flex circuit to a second surface of the layer of piezoelectric material to form an assembly. The assembly is attached to the non-planar top surface of the backing block.

According to a third aspect of the present invention, there is provided a transducer array for transmitting and receiving ultrasound. The transducer array includes a support having a non-planar surface in an elevation direction and a plurality of transducer elements located on said non-planar surface. A plurality of kerfs defining elements extend into the support. The plurality of element-defining kerfs separate each transducer element from one another along an azimuthal direction.

FIGS. *4a–4e* illustrate a step in the manufacture of the transducer array according to several preferred embodiments of the present invention.

Figure 5:
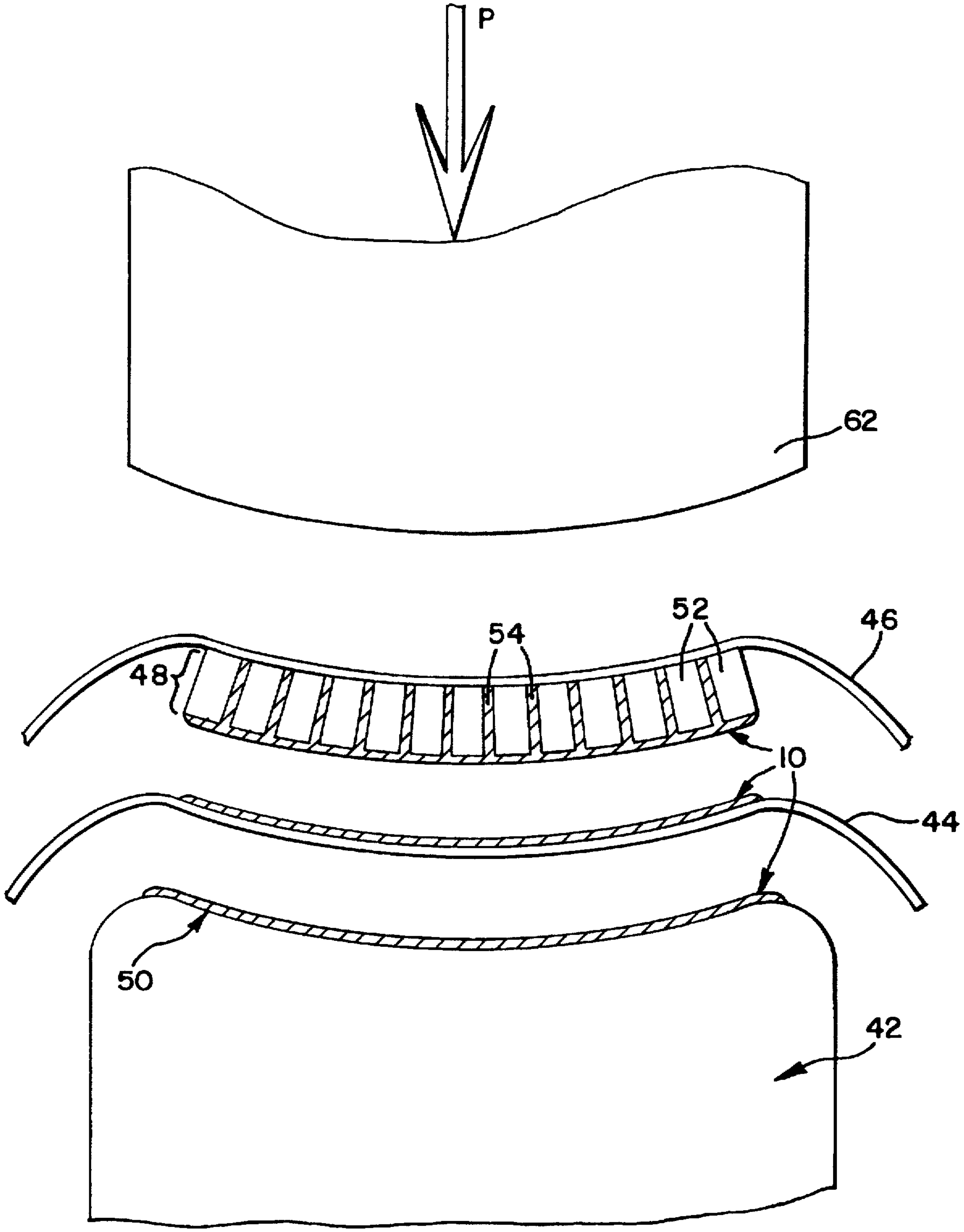

FIG. 5 illustrates a subsequent step in the manufacture of the transducer assembly.

FIG. *6a* illustrates a cross-sectional view of the transducer array showing the profile of an elevational kerf formed in the backing block according to a first preferred embodiment.

FIG. *6b* illustrates a cross-sectional view of the transducer array showing the profile of an elevational kerf formed in the backing block according to a second preferred embodiment.

FIGS. *7a* and *7b* illustrate a cross-sectional views of the transducer array according to still other preferred embodiments of the present invention.

Figure 8:
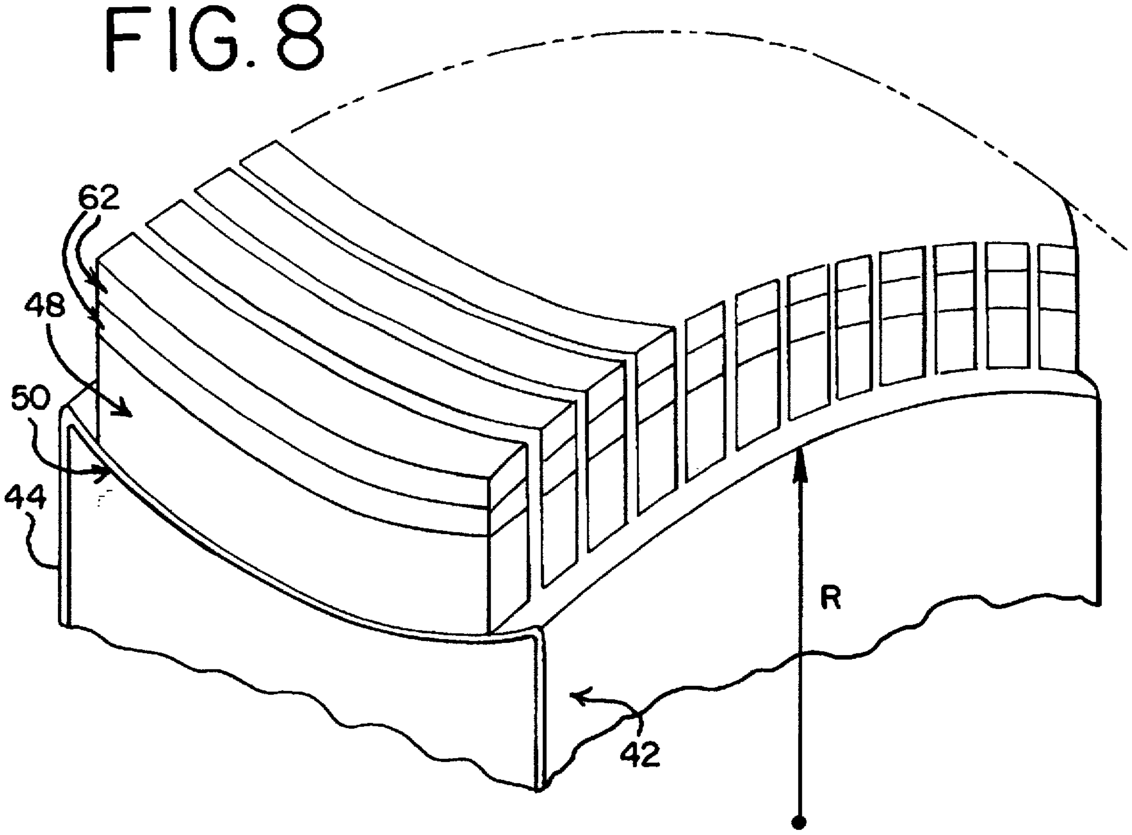

FIG. 8 illustrates a perspective view of a transducer array according to another embodiment of the present invention.

Figure 9:
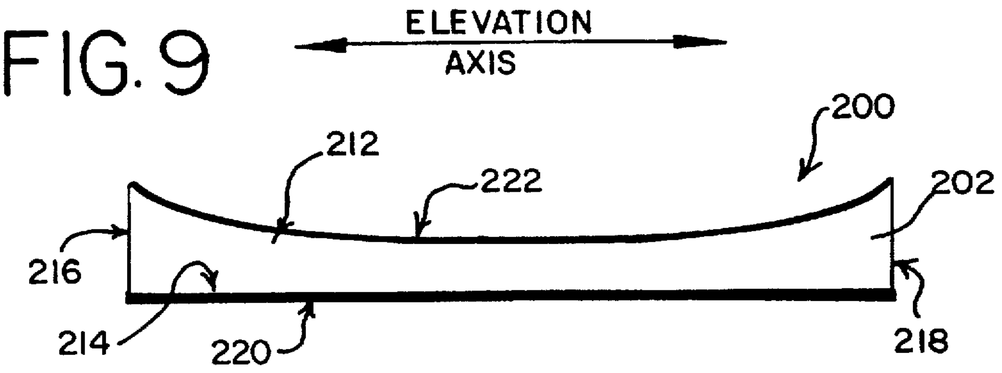

FIG. 9 illustrates a step in the manufacture of a transducer array according to another preferred embodiment in which the piezoelectric layer is of non-uniform thickness.

Figure 10:
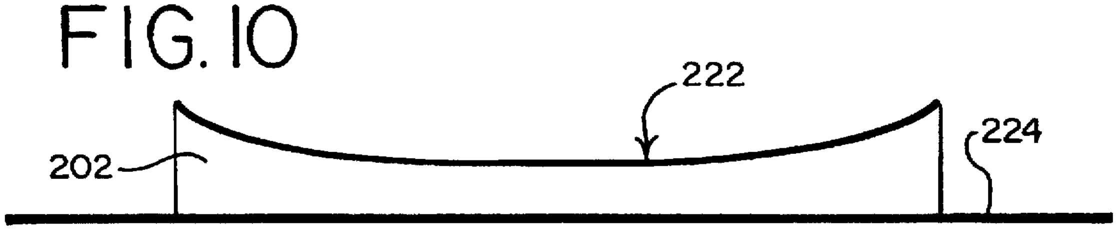

FIG. 10 illustrates a subsequent step in the manufacture of the piezoelectric layer having nonuniform thickness shown in FIG. 9.

Figure 11:
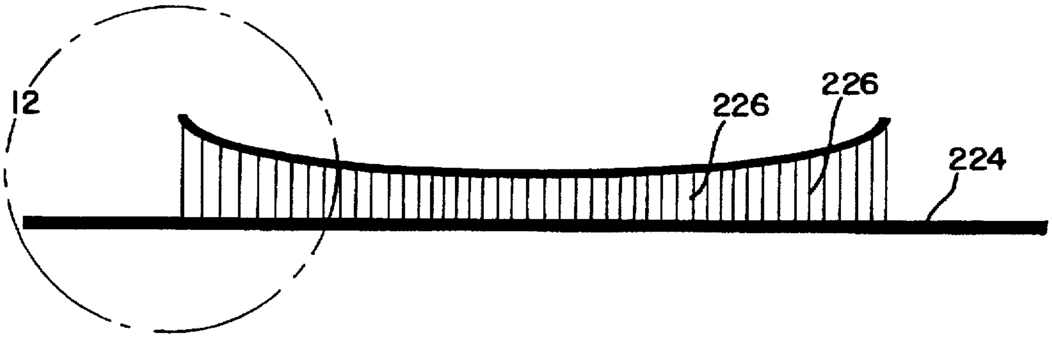

FIG. 11 illustrates a further subsequent step in the manufacture of the piezoelectric layer shown in FIG. 9.

Figure 12:
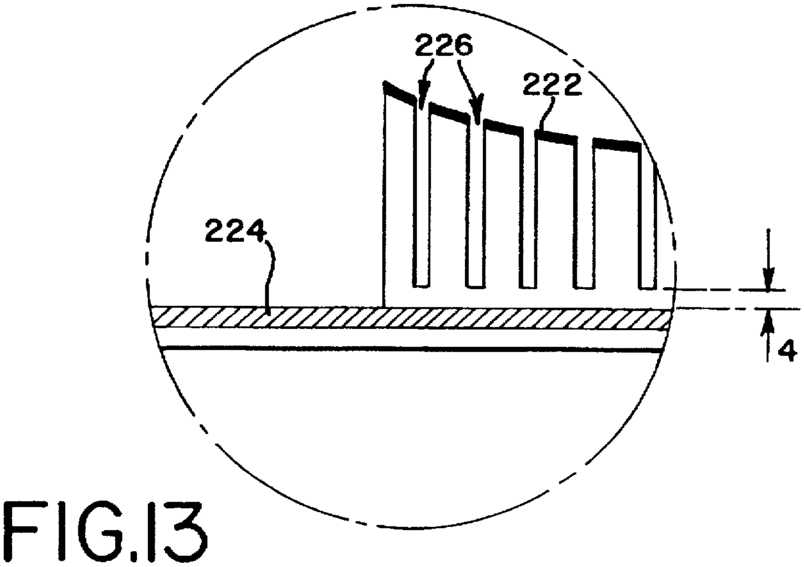

FIG. 12 is an exploded view of a portion of the transducer segment shown in FIG. 11.

Figure 13:
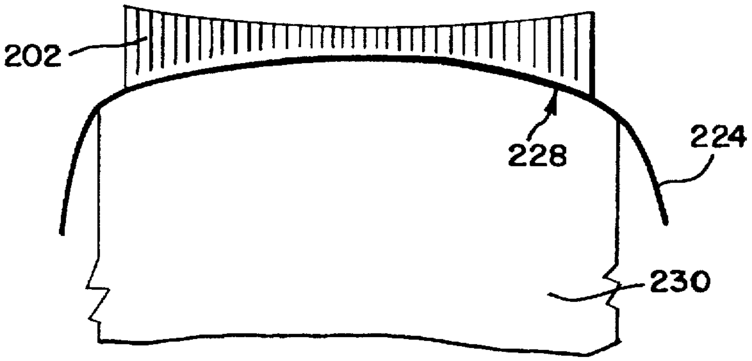

FIG. 13 is a schematic of the piezoelectric layer shown in FIG. 9 mounted on a prefabricated backing block.

DETAILED DESCRIPTION OF THE PRESENTLY PREFERRED EMBODIMENTS

Figure 1:
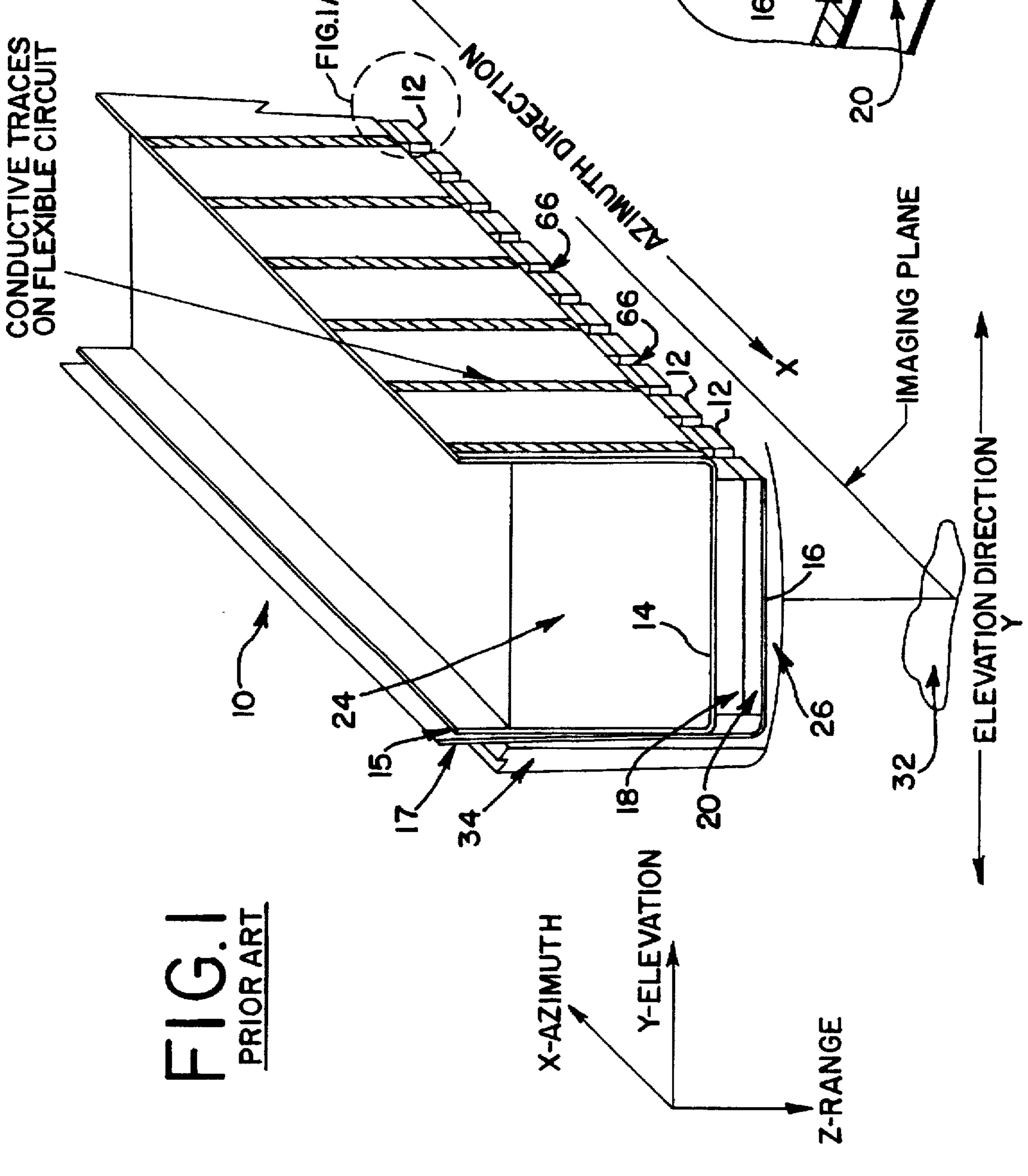
FIG.1 PRIOR ART
FIG. 1 illustrates a prior art transducer array for transmitting and receiving an ultrasound beam.
Figure 1A:
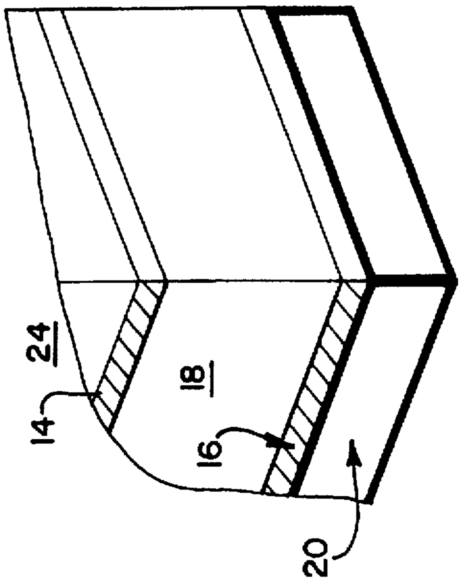
FIG. 1A is an exploded view of an element of the transducer array shown in FIG. 1.

FIG. 1 generally illustrates a transducer array 10 for transmitting and receiving an ultrasound beam. Typically, such an array may have 128 transducer elements 12 arranged along the indicated azimuthal direction. Adapted from radar terminology, the indicated x, y, and z directions are referred to as the azimuthal, elevation, and range directions, respectively.

Each transducer element 12, typically rectangular in azimuthal cross-section, may comprise a first electrode 14, a second electrode 16 and a poled piezoelectric layer 18. In addition, one or more acoustic matching layers 20 may be disposed over the piezoelectric layer 18 to increase the efficiency of the sound energy transfer to and from the external medium. The electrode 14 for a given transducer element 12 may be part of a flexible circuit 15 for providing the hot wire or excitation signal to that piezoelectric element 12. Electrode 16 for a given transducer element may be connected to a ground return 17. FIG. *1a* is an exploded view of a portion of a transducer segment shown in FIG. 1. To further increase performance, the piezoelectric layer 18 may be plated or metalized on its top and bottom surfaces (not shown) and the matching layer 20 may also be plated or metalized over the edge surfaces so that electrode 16 which is in physical contact with the matching layer 20 is electrically coupled to a surface of the piezoelectric layer 18 via the matching layer plating.

The transducer elements 12 are disposed on a support or backing block 24. The backing block 24 should be highly attenuative such that ultrasound energy radiated in its direction (i.e., away from an object 32 of interest) is substantially absorbed. In addition, a mechanical lens 26 may be placed on the matching layer 20 to help confine the generated beam in the elevation-range plane and focus the ultrasound energy to a clinically useful depth in the body. The transducer array 10 may be placed in a nose piece 34 which houses the array. Examples of prior art transducer structures are disclosed in Charles S. DeSilets, *Transducer Arrays Suitable for Acoustic Imaging*, Ph.D. Thesis, Stanford University (1978) and Alan R. Selfridge, *Design and Fabrication of Ultrasonic Transducers and Transducer Arrays*, Ph.D. Thesis, Stanford University (1982).

Individual elements 12 can be electrically excited by electrodes 14 and 16 with different amplitude and time and/or phase characteristics to steer and focus the ultrasound beam in the azimuthal-range plane. An example of a phased array acoustic imaging system is described in U.S. Pat. No. 4,550,607 issued Nov. 5, 1985 to Maslak et al. and is specifically incorporated herein by reference. U.S. Pat. No. 4,550,607 illustrates circuitry for combining the incoming signals received by the transducer array to produce a focused image on the display screen. When an electrical signal pulse is imposed across the piezoelectric layer 18, the thickness of the layer momentarily changes slightly. This property is used to generate acoustic energy from electrical energy. Conversely, electrical signals are generated across the electrodes in contact with the piezoelectric layer 18 in response to thickness changes that have been imposed mechanically by reflecting acoustic waves returning from the body.

The pressure waves generated by the transducer elements 12 are directed toward an object 32 to be observed, such as the heart of a patient being examined. Each time the pressure wave confronts tissue or anything having a different acoustic impedance, a portion of the wave is reflected backward. The array of transducers may then convert the reflected pressure waves into corresponding electrical signals. These electrical signals are then combined to produce a focused image as described in U.S. Pat. No. 4,550,607.

For the transducer shown in FIG. 1 the beam is said to be lens focused in the elevation direction. The focusing of the beam in the azimuthal direction is done electronically by controlling and staggering the timing of the transmissions of each transducer element in the transmit mode. This may be accomplished by introducing appropriate phase delays in the firing signals.

Reflected energy from a particular location in the imaging plane is collected by the transducer elements. The resultant electronic signals from individual transducer elements are individually detected and summed with the others after introducing appropriate delays and apodization to achieve focusing. Extensive processing of such data from the entire imaging plane is done to generate an image of the object. Such an image is typically displayed on a CRT display monitor in real time at 10–30 frames/second.

Figure 2:
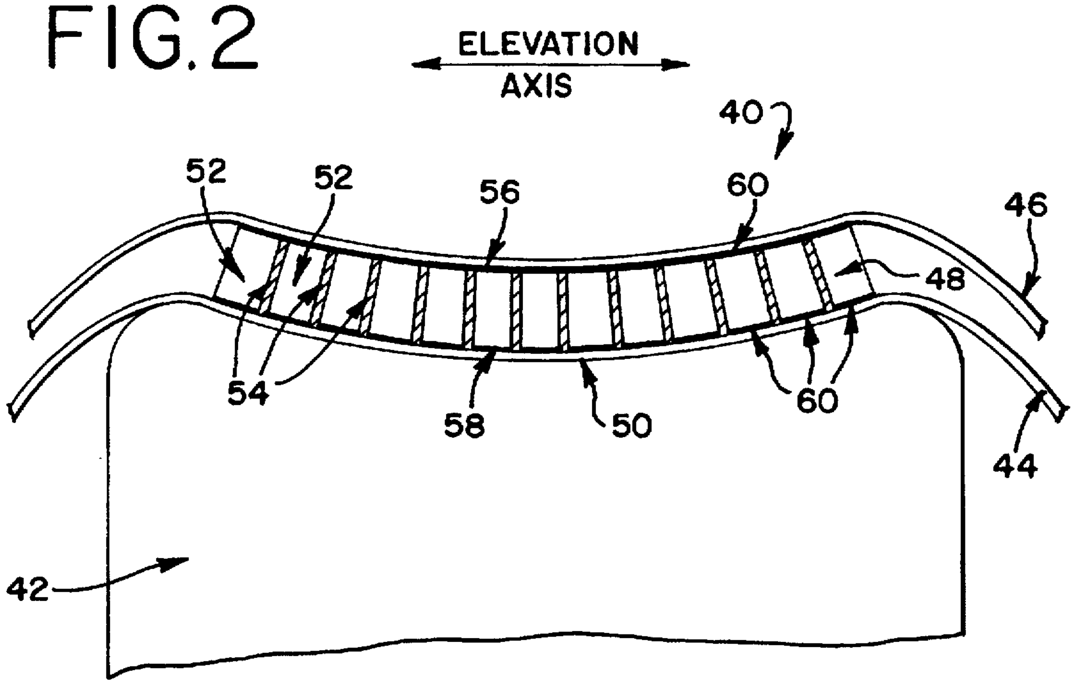
FIG. 2 illustrates a cross-sectional view of a transducer array according to a first preferred embodiment of the present invention.

FIG. 2 illustrates a cross-sectional view of a transducer array according to a first preferred embodiment of the present invention. The cross-section is taken along the elevation direction. The transducer array 40 includes a backing block 42, a first interconnecting flex circuit 44, a second interconnecting flex circuit 46, and a layer of piezoelectric material 48. In a preferred embodiment, flex circuit 44 includes a patterned signal electrode and flex circuit 46 includes an unpatterned ground electrode. Preferably, the top surface 50 of the backing block 42 which faces the object to be imaged is non-planar or curved. In a more preferred embodiment, the top surface 50 is concave to the patient as shown. Azimuthal bending kerfs 54 have been diced into the piezoelectric crystal layer 48 to create a plurality of piezoelectric subcrystals 52. The number of subcrystals 52 may, for example, range in number from 32 to 256 along the elevation direction. In a preferred embodiment, a piezoelectric material which is commonly used in ultrasound transducers, lead zirconate titanate (PZT), is used to form piezoelectric crystal layer 48. In a preferred embodiment PZT known as D32034HD commercially available from Motorola Ceramic Products or Albuquerque, New Mexico of PZT-5H commercially available from Morgan Matroc, Inc. of Bedford, Ohio may be used. Other piezoelectrics or electrostrictives may be used. Alternatively, an elevationally bendable prefabricated composite material or PVDF polymer material may replace the piezoelectric crystal layer 48. As will be described in detail, the azimuthal bending kerfs 54 may be filled with an epoxy.

Alternatively, if the piezoelectric layer is made thin enough the bending kerfs are not necessary and the material is flexible enough to bend without the bending kerfs.

Each piezoelectric subcrystal 52 has a top surface 56 and bottom surface 58 on which are formed on material 48 electrodes 60. The electrodes 60 are formed before the subcrystals 52 are laminated to the backing block 42 as will be described hereinafter. In a preferred embodiment the electrodes 60 are formed of a metallic material such as nickel or gold. The electrode 60 on the top surface 56 of each piezoelectric subcrystals 52 is in contact with ground flex circuit 46 and the electrode 60 on the bottom surface 58 of each piezoelectric subcrystals 52 is in contact with the signal flex circuit 44 which is arranged to have a dedicated electrical trace for each element in the azimuthal direction. It is to be noted that each element consists of multiple subcrystals 52 arranged along a curved path in the elevation/range plane. Electrical signals are selectively applied across each piezoelectric element by imposing a voltage across signal flex circuit 44 and ground flex circuit 46.

In a preferred embodiment, the backing block 42 is formed of an acoustically attenuative material which absorbs acoustical energy radiated into it and prevents that energy from being radiated back to the body to avoid reverberation artifacts in the image. In a preferred embodiment, the backing block may be comprised of a filled epoxy Dow Corning part number DER 332, Dow Corning curing agent DEH 24 and an aluminum oxide filler to adjust the impedance.

Figure 3:
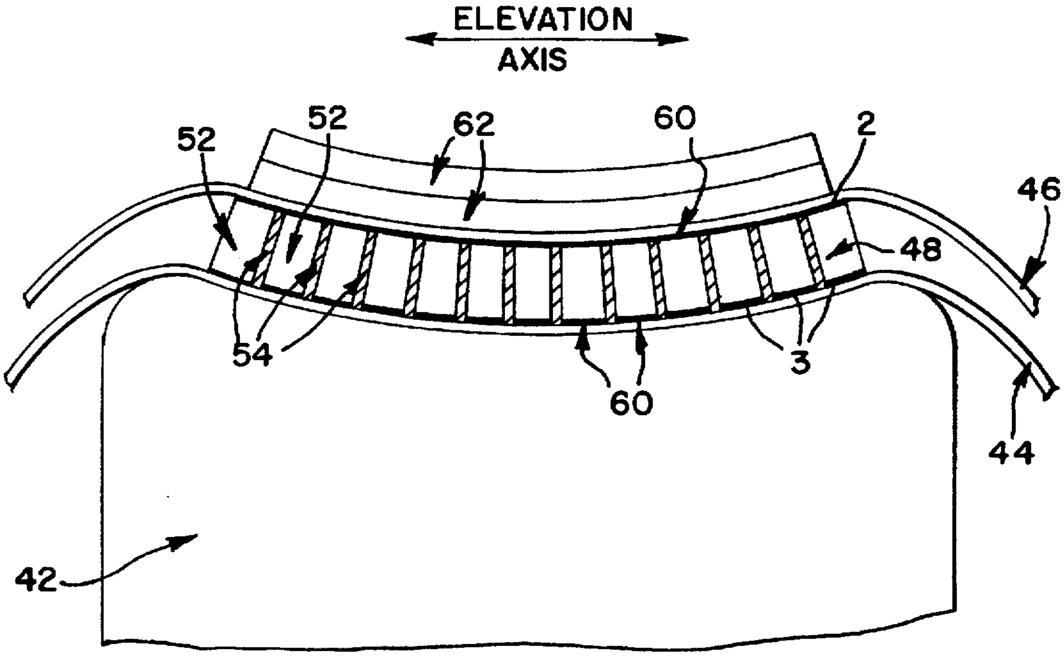
FIG. 3 illustrates a cross-sectional view of a transducer array according to a second preferred embodiment.

FIG. 3 illustrates a cross-sectional view of a transducer array according to a second preferred embodiment. The cross-sectional view is taken along the elevation direction. The transducer array shown in FIG. 3 is similar to that shown in FIG. 2, however, acoustic matching layers 62 have been added. The acoustic matching layers 62 are disposed above the transducer array and more specifically the acoustic matching layers 62 are disposed on top of ground flex circuit 46. While two acoustic matching layers are illustrated, the present invention is not limited to a particular number of matching layers. There may be only one acoustic matching layer 62 provided or two or more acoustic matching layers. The acoustic matching layers 62 are provided to impedance match the piezoelectric material to the object being imaged so that a maximum amount of acoustic energy couples into the object being imaged. Conversely, when an acoustic wave is incident to the transducer, matching layers allow that signal to be absorbed by the transducer with minimum reflection. It is important to minimize the reflection since it may cause reverberation artifacts in the image. In a preferred embodiment the matching layers are formed of at least one filled polymer and have impedances between that of the PZT and patient.

The series of azimuthal bending kerfs 54 formed in the piezoelectric crystal layer 48 allow the piezoelectric crystal layer 48 to be flexed and curved in the elevation direction as shown. The bending kerfs 54 also reduce the acoustic impedance of the piezoelectric crystal layer 48 thereby allowing a better impedance match between the piezoelectric crystal layer 48 and the human body into which the sound waves are radiated. A better match improves the efficiency of the transducer over a wider frequency range.

The backing block 42 and the acoustic matching layers 62 may be formed using a thermosetting polymer material such as an epoxy or urethane. The acoustic impedance of the backing block 42 and acoustic matching layers 62 can be adjusted by adding fillers such as aluminum oxide or tungsten. The impedance of these materials should be optimized to maximize the acoustic output and the reflectivity of the transducer over a wide frequency range. Depending upon the amount of piezoelectric material removed by the bending kerfs 54, and the required frequency bandwidth and band shape, the optimum impedance of the backing block 42 may be between 3–10 MRayls and that of the acoustic matching layers 62 may be between 5–10 MRayls for the matching layer closest to the piezoelectric material between 2–4 MRayls for the matching layer closest to the body being imaged.

The signal flex circuit 44 and ground flex circuit 46 are manufactured using well known combinations of conductive metallic foils and insulating films and generally consist of a single such conductive layer and at least one insulating layer such as KAPTON™. A typical flex circuit is manufactured using one-ounce copper foil which is coated or laminated to 0.001" insulating films of polyimide, such as KAPTON™. These layers can be individually patterned so that the signal flex circuit 44 has an exposed lead for each transducer element in the array and a connection is made between the piezoelectric material, bottom electrode 60 and signal flex circuit 44. Similarly, connection is made between the piezoelectric material, top electrode 60 and ground flex circuit 46. Flex circuits such as the signal flex circuit 44 and ground flex circuit 46 can be manufactured by Sheldahl of Northfield, Minn. The KAPTON™ layers insulate hot leads from ground leads where necessary and provide alignment guides and support. In a preferred embodiment, the portion of the signal flex circuit 44 that is in contact with electrode 60 extends over the entire surface of the electrode 60.

Because the signal flex circuit 44 is preferably formed of copper, the copper acts to draw out heat generated from the piezoelectric crystal layer 48. Of course, materials other than the copper layer and polyimide materials may be used to form the signal flex circuit 44 and ground flex circuit 46. The signal flex circuit 44 may comprise any interconnecting design used in the acoustic or integrated circuit fields, including solid core, stranded, or coaxial wires bonded to an insulating material and conductive patterns formed by known thin-film, thick-film or conductive ink printing processes.

An insulating layer (not shown) overlies the array and is placed between the acoustic matching layers 62 and the object (body) being imaged to protect the patient. In a preferred embodiment, this insulating layer is made of a soft polymer such as a urethane. The insulating layer also serves other purposes including protecting the transducer from the environment in which the transducer is placed which may contain scanning gels, disinfectants, etc. In addition, the insulating layer is shaped to mechanically improve the transducer/patient acoustic contact interface. An important consideration is that this insulating layer be close to the acoustic impedance of the object being imaged, that it have low attenuation of acoustic energy, and velocity similar to the body.

Figure 4A:
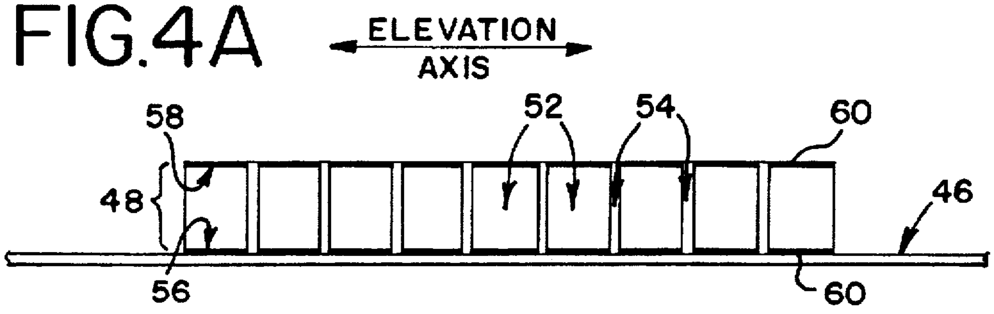

A method of manufacturing the transducer arrays shown in FIGS. 2 and 3 will now be described beginning with reference to FIGS. 4*a* and 4*b*. With reference to FIG. 4*a*, the first step is to attach the piezoelectric crystal layer 48 to the ground flex circuit 46. While the piezoelectric crystal layer 48 is shown having azimuthal bending kerfs 54 formed therein, the kerfs 54 are preferably, but not necessarily, formed after the piezoelectric layer 48 has been laminated to ground flex circuit 46. For fabrication, piezoelectric crystal layer 48 has been flipped upside down from its orientation shown in FIGS. 2 and 3. The piezoelectric crystal layer 48 is chosen to have a resonant thickness appropriate to produce the desired frequency range of the transducer array. In a preferred embodiment the frequency of operation of such transducers range from about 2 MHz to 10 MHz. The thickness of the piezoelectric layer 48 for these frequencies would range from about 0.004 inches to 0.024 inches. As previously described, the top and bottom surfaces 56 and 58 of the piezoelectric crystal layer 48 each have an electrode 60 formed thereon. The electrode 60 on the top surface 56 is electrically isolated from the electrode 60 on the bottom surface 58. The electrodes 60 are preferably formed primarily of gold or nickel and can be predeposited on the top and bottom surfaces of the piezoelectric crystal layer 48 using chemical plating or vacuum processes such as sputtering or evaporation, for example. The electrical connection between the electrode 60 on the top surface of the piezoelectric crystal layer 48 and ground flex circuit 46 can be formed in numerous well known ways including the use of epoxy or soldering. In a preferred embodiment, the portion of the ground flex circuit 46 in contact with the electrode 60 on the bottom surface of the piezoelectric crystal layer 48 is coextensive in size therewith. Electrical connection is made between the flex circuit and the piezoelectrical crystal through a very thin layer of non-conductive epoxy.

Figure 4B:
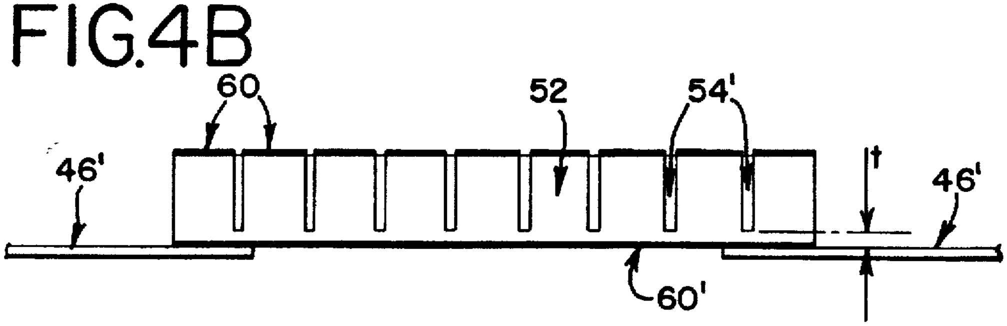

FIG. 4*b* illustrates an alternative preferred embodiment of the present invention. In FIG. 4*b* the ground flex circuit 46' does not extend across the entire elevation width of the piezoelectric crystal layer 48 as shown in FIG. 4*a*. Instead, ground flex circuit 46' is connected only at the ends of the metalized piezoelectric crystal layer 48.

With respect to both FIGS. 4*a* and 4*b*, once the piezoelectric crystal layer 48 is connected to ground flex circuit 46 or 46', the azimuthal bending kerfs 54 or 54' can be formed. The bending kerfs 54 or 54' may be formed using a dicing saw with a thin blade or with a laser such as a $CO_2$ or excimer laser. The kerfs 54 and 54' extend along the entire azimuthal axis of the piezoelectric crystal layer 48 (i.e. into the paper) which allows for flexibility of the piezoelectric layer in the elevation range plane of the paper. In a preferred embodiment with reference to FIG. 4*a*, the kerfs 54 are made to a depth which completely separates the piezoelectric crystal layer 48 into individual piezoelectric subcrystals 52 without cutting through ground flex circuit 46. In another preferred embodiment shown in FIG. 4*b*, the bending kerfs 54' do not extend through the entire thickness of the piezoelectric crystal layer 48. Preferably a thickness of about 0.003 inches or less is left of the piezoelectric crystal layer 48 under the bending kerfs 54'. Thus the electrode 60 on the top surface 56 of the piezoelectric crystal layer 48 remains continuous and connects ground flex circuit 46' connected at one end of the piezoelectric layer to the ground flex circuit 46' connected at the other end of the piezoelectric layer.

Figure 4C:
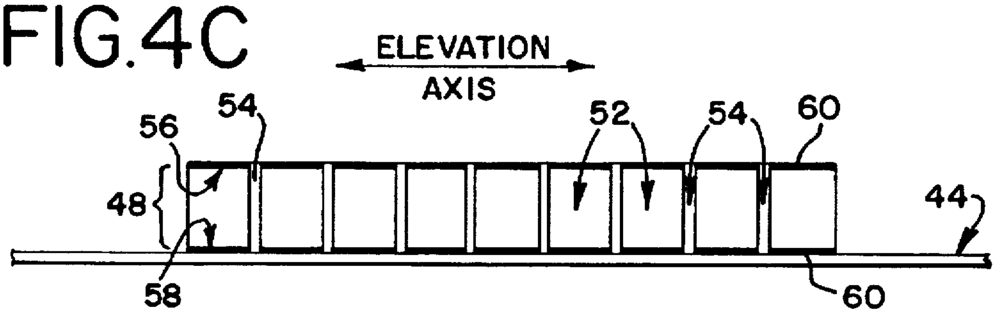

FIG. 4*c* illustrates still another alternative preferred embodiment of the present invention. In FIG. 4*c* the piezoelectric layer 48 is bonded to the signal flex circuit 44. Like the embodiment shown in FIG. 4*a*, the azimuthal bending kerfs 54 extend through the top and bottom electrodes but not the signal flex circuit 44.

Figure 4D:
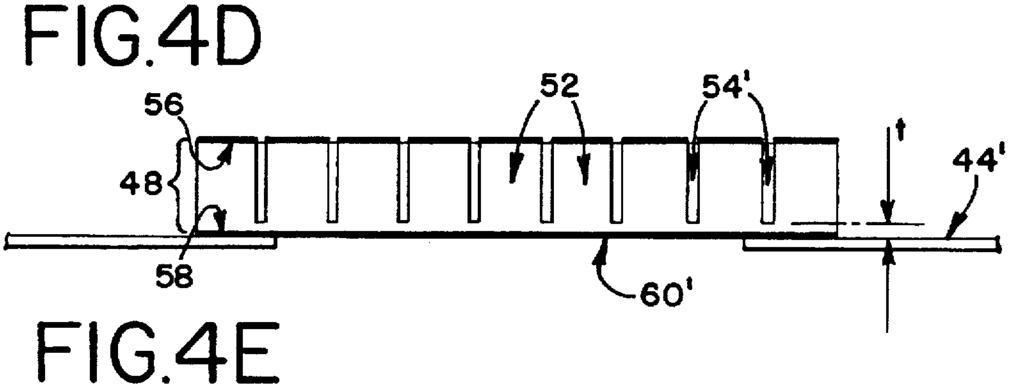

FIG. 4*d* illustrates another alternative preferred embodiment similar to that shown in FIG. 4*b* except the piezoelectric layer 48 is bonded to the signal flex circuit 44' which in this embodiment only contacts the piezoelectric layer at the ends. In this preferred embodiment the azimuthal bending kerfs 54' do not extend through bottom electrode 60' as for the earlier FIG. 4*b*.

Figure 4E:
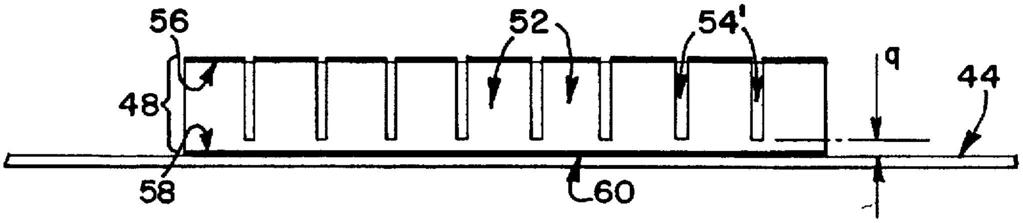

FIG. 4*e* illustrates still another alternative preferred embodiment of the present invention similar to that shown in FIG. 4*c* except the azimuthal bending kerfs 54' do not extend through bottom electrode 60 of piezoelectric layer 48.

Alternatively the elevational bending kerfs can be formed and filled in a separate process using traditional composite dice and fill methods. In this case the composite piezoelectric can be directly laminated to the ground or signal flex circuit. During the elevational curving described next the composite piezoelectric may need to be heated to a moderately high temperature, about 65° C., to soften the kerf filler epoxy to allow bending.

The removal of copper in the central portion of the piezoelectric as shown in FIGS. 4*b* and 4*d* eliminates several interfaces between transducer components in the final transducer assembly. This has the advantage of creating fewer acoustic internal reflections, improves overall reliability of the transducer by lowering the number of interfaces which can fail by delamination and also results in transducer designs with thicker piezoelectric components. The thicker components are advantageous in a manufacturing environment. The disadvantage of the assemblies shown in FIGS. 4b and 4d is that the removal of the copper makes it a more difficult sub-assembly to handle and also creates a step on the piezoelectric surface which must be accounted for in later lamination steps by having machined cutouts in the matching layer or backing block components next to the piezoelectric layer.

The next step illustrated in FIG. 5 is to bend or form the subassembly of the piezoelectric crystal layer 48 and flex circuit 46 into the desired curved shape. The subassembly is formed to the desired shape while simultaneously forming and attaching it and signal flex circuit 44 to the concave backing block 42. In a preferred embodiment, the piezoelectric layer 48 is bonded to ground flex circuit 46 as shown in FIG. 4a and then the azimuthal bending kerfs 54 are formed in the piezoelectric layer 48. A low viscosity epoxy 10 is applied to all mating surfaces, i.e. top concave surface 50 of the backing block 42, signal flex circuit 44, and piezoelectric crystal layer 48. In a preferred embodiment, the epoxy is allowed to fill bending kerfs 54 formed in the piezoelectric crystal layer 48. In a preferred embodiment, the signal flex circuit 44 is placed on the top curved surface of the backing block 42 and the bottom surface of the piezoelectric crystal layer 48 is placed on top of the signal flex circuit 44. As shown in FIG. 5, pressure P is applied with a compliant external pad or pressurization member 62 to ensure intimate contact between components 42, 44, 48/46 and 10. The pressure is maintained until the epoxy is set. This usually takes 24 hours if using a typical room temperature epoxy such as Hysol resin RE2039 and hardener HD3561 available from Hysol of Industry, California.

If desired, the entire assembly can be raised to a moderate temperature such as to 65° C. to accelerate the curing of the epoxy. If an acoustic matching layer or layers are also to be included they may be affixed at the same time as the other components are assembled or they may be affixed in a separate later or earlier process step. The acoustic matching layer(s) as previously discussed, are flexible and thus can be bent to the desired shape by applying gentle pressure. The same epoxy can be used and the same compliant member 62 can be used to shape and affix the acoustic matching layer(s).

While the assembly step shown in FIG. 5 was illustrated using a piezoelectric layer bonded to a ground flex circuit 46 as shown in FIG. 4a, other combinations are possible. Thus, once the piezoelectric layer 48 has been bonded to either ground flex circuit 46 or 46' as shown in FIGS. 4a and b or signal flex circuit 44 or 44' as shown in FIGS. 4c–e and the azimuthal bending kerfs 54 are diced partially or entirely through the piezoelectric layer 48, the assemblies shown in FIGS. 4a–e can be laminated to the curved backing block 42 in any orientation, i.e. upright or upside down. In a preferred embodiment, the signal flex circuit 44 is positioned away from the patient, i.e. next to the backing block. Thus, the structures in FIGS. 4a and 4b would be flipped before lamination and those in FIGS. 4c–e would not be flipped before lamination.

The next step is to create a plurality of transducer elements. New element defining kerfs 66 (see FIG. 1) are made along the elevation direction to separate the piezoelectric layer 48, signal and ground flex circuits 44 and 46 into a plurality of individually electronically addressable transducer elements in the azimuthal direction. In a preferred embodiment a dicing saw with a diamond impregnated blade is used to cut through the ground flex circuit 46, piezoelectric crystal layer 48, signal flex circuit 44 and somewhat into the backing block 42. The blade is typically between about 15 and 75 microns wide (or thick). Preferably the transducer elements have a width in the azimuthal direction of between about 60 to 160 microns.

Figure 6A:
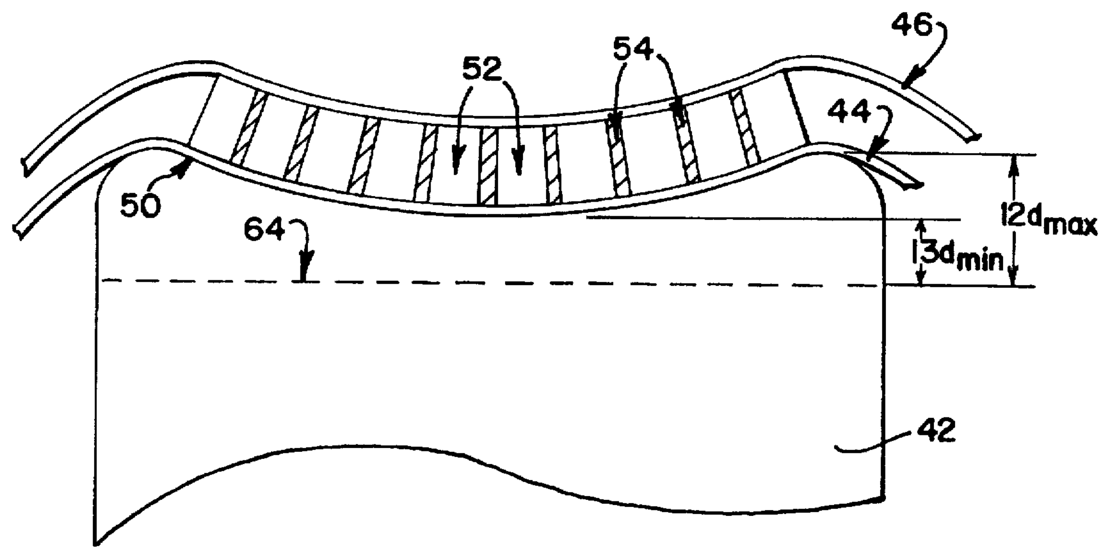
Figure 6B:
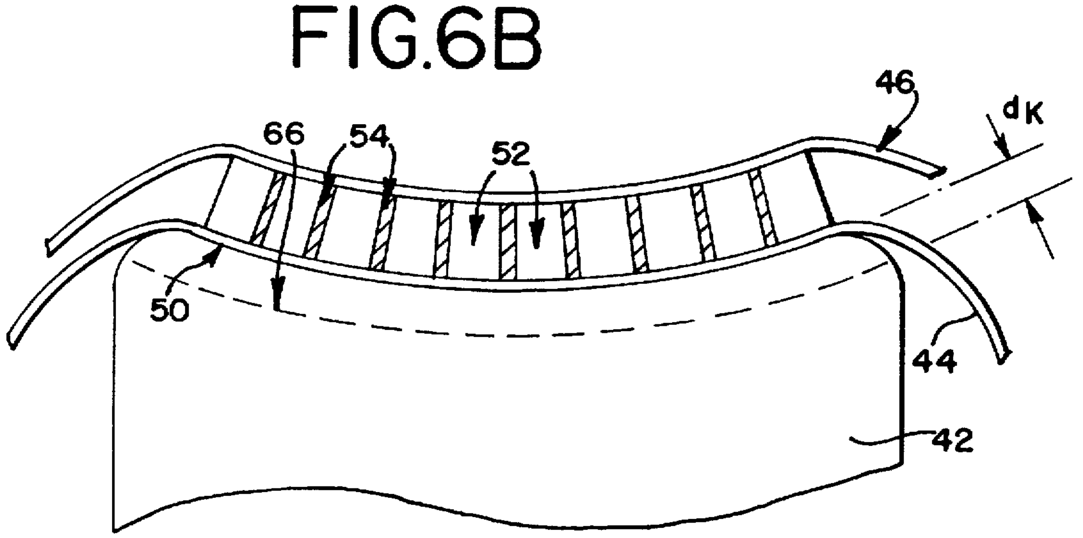
Figure 7A:
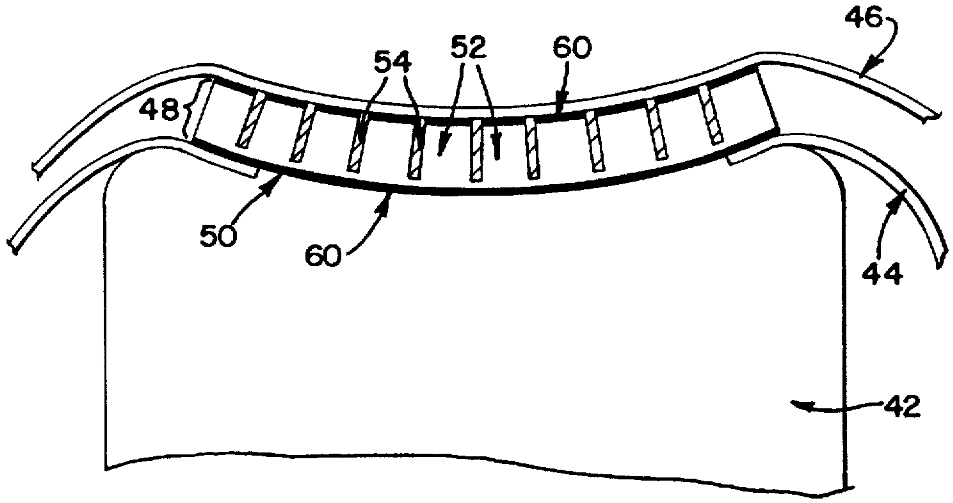
Figure 7B:
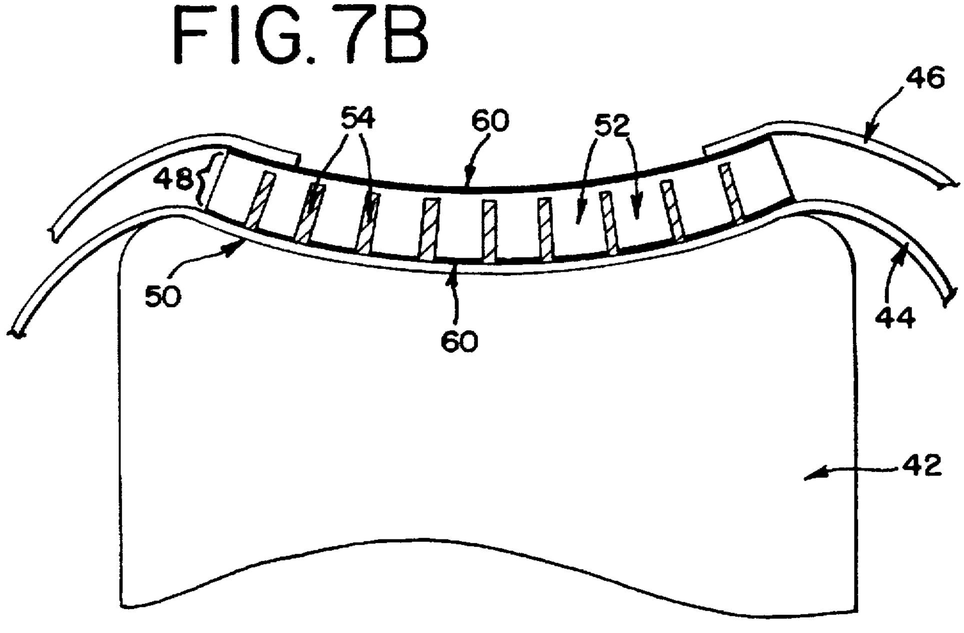

FIGS. 6a and 6b each illustrate a cross-sectional view of the transducer array showing the profile of the elevational element definitional kerfs 64 and 66 formed in the backing block 42 according to two preferred embodiments. In the preferred embodiment as shown in partial cross-section in FIG. 6a, the depth of the definitional kerf 64 is straight across the backing block 42 resulting in a variable depth kerf with reference to the top surface 50 of the backing block 42 where the kerf 64 has a minimum depth $d_{min}$ (13) and a maximum depth $d_{max}$ (12). Depending on the frequency of operation of the transducer, and the radius of curvature of the backing block surface 50 $d_{min}$ can range from about 0 to 0.020 inches and $d_{max}$ can range from about 0.005 to 0.030 inches. In another embodiment as shown in FIG. 6b, the depth of the element definitional kerf 66 generally follows the profile of the top surface 50 of the backing block 42 so that the depth of the kerf 66 with reference to the top surface 50 of the backing block 42 is substantially constant. Either shape of the kerfs 64 or 66 formed in the backing block 42 helps to minimize unwanted acoustic crosstalk between adjacent transducer elements.

Next, if desired, a radio frequency interference shield (not shown) can be bonded or joined to the ground flex circuit 46 or matching layers if used. This shield may consist of a polymeric material that has been sputtered with a metallic film material which is electrically attached to the ground flex circuit 46. Preferably a very thin material polymeric material less than 0.0005" thick is used with a metallic film which is less than 20 microinches thick. In one preferred embodiment the material used to bond this shield to the transducer assembly can be allowed to flow into the element elevational isolating kerfs and it is a soft material such as urethane or silicone rubber. In another preferred embodiment a very thin layer of epoxy can be used to bond the shield taking care to make sure the epoxy does not flow into the diced kerfs. This leaves the kerfs primarily air filled which gives the greatest acoustic isolation between adjacent elements.

Next a soft polymer spacer and sealing layer (not shown) can be bonded or joined upon ground flex circuit 46 or upon an acoustic matching layer or the RFI shield if there is one. Because this polymer has about the same acoustic velocity as the patient being imaged and has low sound attenuation at the frequencies being used, it does not significantly absorb or focus the sound energy. In a preferred embodiment, the polymer layer is cast or molded directly on the assembly and can be used to seal the transducer array into a probe housing (not shown). In a preferred embodiment a urethane, preferably, Castall 2008 by Castall of Massachusetts is used. Alternatively, a previously molded, machined or cast spacer material made out of, for example epoxy, or polycarbonate can be attached using a thermosetting material such as an epoxy or urethane. The same care as previously mentioned of keeping the bonding material out of the kerfs must be taken. The transducer housing (not shown) and the profile of the polymer layer are shaped to provide access to the patient being imaged while optimizing the patient's comfort level.

It is important that the spacing and sealing layer adhere to the transducer array and protect it from the scanning gels and disinfectants used during use. In a preferred embodiment where a gold metallized RFI shield is used several adhesion promoting layers are used and have been shown to improve the resistance of the transducer array to gels and disinfectants. U.S. Patent Application entitled "Improved Coupling of Acoustic Window and Lens for Medical Ultrasound Transducers and Method for the Manufacture Thereof" by J. Talbot et al. filed concurrently herewith (attorney docket no. 5050/91) which is specifically incorporated herein by reference describes various structures and methods for promoting adhesion between RFI shields and lens or windows.

FIGS. *7a* and *7b* illustrate cross-sectional views of the transducer array according to a third and fourth preferred embodiment of the present invention. In both FIGS. *7a* and *7b*, the reduced copper transducer assemblies shown in FIGS. *4b* and *4d* are depicted. In FIG. *7a*, the transducer array is positioned so that the bottom surface of the piezoelectric crystal layer 48 and electrode 44 are in contact with the top surface 50 of the backing block 42. The flex circuit 46 extends over the piezoelectric crystal layer 48. In FIG. *7b*, the flex circuit 44 is positioned on the top surface 50 of the backing block 42. The method of making the transducer assemblies shown in FIGS. *7a* and *7b* are the same as previously described and thus need not be described again. In addition, element definitional kerfs 64 or 66 extending along the elevation direction as shown in FIGS. *6a* and *6b* also can be formed in the transducer assembly.

FIG. 8 illustrates a perspective view of a transducer array according to a preferred embodiment of the present invention. In this preferred embodiment, the backing block is not only curved in the elevation direction but it is also curved in the azimuthal direction as shown. This type of array, commonly referred to as a curved linear array has the advantage of a wider field of view of the body being imaged due to the curvature in the azimuth. Depending on the application the radius of curvature along the azimuth can be from about 0.5 inches to 5 inches. One method for creating the curvature in the azimuth is given in U.S. Pat. No. 4,734,963 which is hereby specifically incorporated by reference. In particular, a thin material backing block is used and the signal flex circuit, piezoelectric material and ground flex circuit are mounted on the backing block as previously described according to the method of the present invention. The element defining kerfs are then diced. To curve the array in the azimuthal direction, a rigid backing block having such a curvature is inserted under the flexible backing block to cause the array to curve in the azimuthal direction.

The transducer array produced according to the described method in this invention creates a transducer array which transfers a maximum amount of acoustic energy to the object or patient being imaged. In addition, this energy is broad banded and allows for the excitation and reception of the array at different frequencies. The higher the excitation frequency, the finer the resolution of the resulting image but the lower the penetration of the sound into the object being imaged. Depending upon the application to which the transducer array is applied, one may want either fine resolution or deep penetration. A transducer assembly that allows for a variety of frequencies to be chosen allows the operator to optimize imaging at any depth, including optimization within a single image frame at various depths.

FIG. 9 illustrates the first step in manufacturing a transducer element according to another preferred embodiment of the present invention. In this preferred embodiment, the transducer elements 200, only one of which is illustrated, have a plano-concave shape. In this preferred embodiment the thickness of the piezoelectric layer 202 varies in the elevation direction. U.S. Pat. No. 5,415,175 issued May 16, 1995 to Hanafy et al., which is specifically incorporated herein by reference, discloses a transducer elements having such a structure.

More particularly, the transducer elements 200 have a front portion 212, a back portion 214, and two sides 216 and 218. The front portion 212 is the surface which is facing the region to be examined. The back portion 214 is generally a planar surface. The front portion 212 is generally a non-planar surface, the thickness of the element 200 being greater at each of the sides 216 and 218 and smaller between the sides. Each element 200 has a maximum thickness LMAX and a minimum or smallest thickness LMIN. Preferably the sides 216 and 218 both are equal to the thickness LMAX and the center of element 200 is at the thickness of LMIN. However, each of the sides 216, 218 do not have to be the same thickness and LMIN does not have to be in the exact center of the transducer element to practice the invention. Although the front portion 212 is illustrated as having a continuously curved surface, front portion 212 may include a stepped configuration, a series of linear segments, or any other configuration wherein the thickness of element 200 is greater at each of the sides 216 and 218 and decreases in thickness at the center, resulting in a negatively "curved" front portion 212.

The layer of piezoelectric material 202 is metalized so that there are individual solid electrodes 220 and 222 on both the flat and the curved surfaces of the piezoelectric layer 202 respectively. The electrodes 220 and 222 are isolated from one another.

The next step shown in FIG. 10 is to couple the flat surface 214 of the piezoelectric layer to a flex circuit 224. Next, bending kerfs 226 are diced into the piezoelectric layer as shown in FIG. 11 and in further detail in FIG. 12. The bending kerfs 226 are diced so that they do not cut through the flex circuit 224 underneath the piezoelectric layer 202. In a preferred embodiment, the bending kerfs 226 do not extend entirely through the piezoelectric layer 202 so that the electrode 220 on the flat surface 214 of the piezoelectric layer remains intact. In a preferred embodiment, the bending kerfs 226 have a width ranging from about 25 to 30 microns with a spacing between kerfs 226 ranging from about 90 to 150 microns.

As previously described, the bending kerfs 226 achieve two purposes. First, the bending kerfs 226, which will be filled with a polymer, create a structure commonly referred to as a composite piezoelectric. Such a composite piezoelectric is acoustically better matched to the other layers in the transducer array thereby enhancing the acoustic output and performance of the transducer array. Secondly, the bending kerfs 226 remove enough of the stiff piezoelectric layer 202 to result in a flexible assembly which can be gently curved without damaging the piezoelectric layer. The assembly of the piezoelectric layer and the flex circuit can now be mounted on a backing block as shown in FIG. 13. The top surface 228 of the backing block 230 is preferably convex in shape. In an alternative embodiment, the top surface of the backing block may be concave in shape. The assembly of the diced piezoelectric layer 202 and flex circuit 224 may then be mounted on the top surface of the backing block along with a ground flex circuit in the same manner as previously described with reference to FIG. 5. Thus the elevational focus of the transducer array can be adjusted by properly selecting the curvature of the top surface of the backing block.

Of course one or more curved matching layers not shown may be disposed on the front portion 212 of transducer element 200. Moreover, the thickness of the matching layers are preferably defined by the equation:

$$LML=(\frac{1}{4})(LE)(CML/CE)$$

where LML is the thickness of the matching layer at a given thickness of the transducer element LE, CML is the sound speed of the matching layer, and CE is the sound speed of the transducer element. Thus, the curvature of the front portion 212 may be different than the curvature of the top portion of the matching layers because the thickness of the matching layer depends on the thickness of the element at the corresponding location. By the addition of matching layers the fraction bandwidth can be improved further and with increased sensitivity due to matching.

The bandwidth increase for a given transducer configuration is approximated by LMAX/LMIN. The bandwidth may be increased just large enough so that there is no need to redesign the already existing hardware for generating the desired frequency activation of the transducer. Typically, this may be an increase in bandwidth of up to 20 percent. Thus, the bandwidth may be increased from zero to 20 percent by increasing the thickness of LMAX relative to LMIN from zero to 20 percent, respectively. For example, if a transducer has an LMAX of 0.012 inches and an LMIN of 0.010 inches, the bandwidth is increased by 20 percent as compared to a transducer having a uniform thickness of 0.010 inches. Preferably, a minor thickness variation of 10 to 20 percent should be utilized. This results in the maximum bandwidth increase, approximately 10 to 20 percent, respectively, without the need to change any of the existing hardware.

In order to receive the full benefit of the invention, that is, increasing the bandwidth greater than 20 percent, it may be necessary to redesign the hardware for exciting the transducer at such a broad range of frequencies. As seen by the above equation, the greater the thickness variation, the greater the bandwidth increase. Bandwidth increases of up to 300 percent for a given design may be achieved in accordance with the principles of the invention. Thus, the thickness LMAX would be approximately three times greater than the thickness LMIN. The bandwidth of a single transducer element, for example, may range from 2 Megahertz to 11 Megahertz, although even greater ranges may be achieved in accordance with the principles of this invention. Because the transducer array constructed in accordance with this invention is capable of operating at such a broad range of frequencies, contrast harmonic imaging may be employed with a single transducer array for observing both the fundamental and second harmonic.

Therefore, by controlling the curvature shape of the transducer element (i.e. cylindrical, parabolic, gaussian, stepped, or even triangular), one can effectively control the frequency content of the radiated energy. In addition, because the signal in the center of the transducer is stronger than at the ends or sides 216 and 218, correct apodization occurs. This is due to the fact that the electric field between the two electrodes on the front portion 212 and bottom portion 214 is greatest at the center of the transducer element 200, reducing side lobe generation.

Further, because the transducer array constructed in accordance with the present invention is capable of operating at a broad range of frequencies, the transducer is capable of receiving signals at center frequencies other than the transmitted center frequency.

The backing block 42 and acoustic matching layers can be manufactured using well-known common epoxies or urethanes as can be purchased from Hysol of Industry, California, for example. Fillers such as aluminum oxide may also be used to control impedance and attenuation. The material impedances can be optimized to provide maximum energy transfer as is commonly practiced. The parallel azimuthal bending kerfs 54 formed in the piezoelectric crystal layer 48 and later filled with epoxy greatly reduces the acoustic impedance of this component. The number, placement and width of bending kerfs 54 may also be adjusted to vary the impedance. This, as well as the acoustic impedance of the acoustic matching layer placed next to the piezoelectric material can be adjusted to maximize the transmission of the acoustic energy through the acoustic matching layers.

It is to be understood that the forms of the invention described herewith are to be taken as preferred examples and that various changes in the shape, size and arrangement of parts may be resorted to, without departing from the spirit of the invention or scope of the claims.

What is claimed is:

1. A transducer for medical ultrasound imaging comprising:
an attenuative prefabricated backing block having a non-planar top surface in an elevation direction wherein said top surface is to be oriented toward the object to be imaged;
a flex circuit disposed on said non-planar top surface;
a piezoelectric layer having a first surface coupled to said flex circuit; and
an electrode coupled to a second surface of said piezoelectric layer.

2. A transducer according to claim 1 further comprising a plurality of bending kerfs extending at least partially into said piezoelectric layer, said plurality of bending kerfs arranged to run along an azimuthal direction.

3. A transducer according to claim 1 wherein said flex circuit is disposed on said piezoelectric layer and said plurality of bending kerfs extend from a top surface of said piezoelectric layer which is in contact with said flex circuit into said piezoelectric layer.

4. A transducer according to claim 1 wherein said flex circuit is disposed under said piezoelectric layer and said plurality of bending kerfs extend from a bottom surface of said piezoelectric layer which is coupled to said flex circuit into said piezoelectric layer.

5. A transducer according to claim 4 wherein said plurality of element defining kerfs have a nonuniform depth with reference to the non-planar top surface of said backing block across said backing block in an elevational direction.

6. A transducer according to claim 1 further comprising a plurality of element defining kerfs extending through said electrode, said piezoelectric layer, said flex circuit and into said backing block wherein said plurality of kerfs extend in an elevation direction.

7. A transducer according to claim 6 wherein said plurality of element defining kerfs have a uniform depth with reference to the non-planar top surface of said backing block across said backing block in an elevational direction.

8. A transducer according to claim 1 further comprising at least one acoustic matching layer disposed over said piezoelectric layer.

9. A transducer according to claim 1 wherein said piezoelectric layer has a uniform thickness.

10. A transducer according to claim 1 wherein said piezoelectric layer is a prefabricate composite.

11. A transducer array according to claim 1 wherein said non-planar surface is concave.

12. A transducer array according to claim 1 wherein said electrode is coupled to opposite ends of said second surface of said piezoelectric layer.

13. A transducer array according to claim 1 wherein said plurality of bending kerfs extend entirely through said piezoelectric layer.

14. A transducer array according to claim 1 wherein said electrode is a flex circuit.

15. A transducer according to claim 1 wherein said attenuative prefabricated backing block has a non-planar top surface in an azimuthal direction.

16. A transducer according to claim 1 wherein said piezoelectric layer has a first electrode on a first surface of the piezoelectric layer, the first electrode being coupled to said flex circuit wherein the flex circuit extends the entire length of the first electrode so as to form a redundant electrical path.

17. A transducer array for medical ultrasound imaging comprising:

a prefabricated support having a non-planar surface in an elevation direction and a plurality of transducer elements located on said non-planar surface; and a plurality of element defining kerfs extending into said support, said plurality of kerfs separating each transducer element from one another along the azimuthal direction.

18. A transducer array according to claim 17 wherein said plurality of element defining kerfs extend a distance into said support wherein the distance is uniform across the elevation with reference to the non-planar surface of said attenuative support.

19. A transducer array according to claim 17 wherein said plurality of element defining kerfs extend a distance into said support wherein the distance is non-uniform across the elevation with reference to the non-planar surface of said attenuative support.

20. A transducer array according to claim 17 wherein said plurality of kerfs have a minimum depth relative to said top surface of said support and a maximum depth relative to said top surface of said support wherein said minimum depth is less than said maximum depth.

21. A transducer for medical ultrasound imaging comprising:

an attenuative prefabricated backing block having a non-planar top surface in an elevation direction wherein said top surface is to be oriented toward the object to be imaged;

a flex circuit disposed on said non-planar top surface;

a piezoelectric layer of uniform thickness having a first surface coupled to said flex circuit, said piezoelectric layer having a plurality of bending kerfs extending into said piezoelectric layer, said plurality of bending kerfs arranged to run along an azimuthal direction; and an electrode coupled to a second surface of said piezoelectric layer.

22. A transducer according to claim 21 wherein said bending kerfs extend partially into said piezoelectric layer.

23. A wide field of view transducer for medical ultra sound imaging comprising:

an attenuative prefabricated backing block having a non-planar top surface in an elevation direction and an azimuthal direction wherein said top surface is to be oriented toward the object to be imaged;

a flex circuit disposed on said non-planar top surface;

a piezoelectric layer of uniform thickness having a first surface coupled to said flex circuit, said piezoelectric layer having a plurality of bending kerfs extending into said piezoelectric layer, said plurality of bending kerfs arranged to run along the azimuthal direction;

an electrode coupled to a second surface of said piezoelectric layer;

at least one acoustic matching layer disposed on said electrode; and a plurality of element defining kerfs extending through said acoustic matching layer, said electrode, said piezoelectric layer, said flex circuit and partially into said backing block, said element defining kerfs arranged to run along the elevation direction.

* * * * *

UNITED STATES PATENT AND TRADEMARK OFFICE

CERTIFICATE OF CORRECTION

PATENT NO. : 5,792,058

DATED : August 11, 1998

INVENTOR(S) : Wendy J. Lee et al.

It is certified that error appears in the above-indentified patent and that said Letters Patent is hereby corrected as shown below:

In column 3, line 57, change "illustrate a cross-sectional" to --illustrate cross-sectional--.

In column 5, line 66, change "subcrystals" to --subcrystal--.

In column 6, line 1, change "subcrystals" to --subcrystal--.

In column 12, line 3, change "elements" to --element--.

In claim 17, line 3, after "prefabricated" insert --attenuative--.

Signed and Sealed this

Twenty-first Day of March, 2000

Attest:

Q. TODD DICKINSON

*Attesting Officer*

*Commissioner of Patents and Trademarks*